United States Patent

Karas et al.

[11] 4,033,171
[45] July 5, 1977

[54] PNEUMATIC DETECTOR FOR CHROMATOGRAPHIC ANALYZER

[75] Inventors: Edwin L. Karas, Sharon, Mass.; Raymond Annino, Coldon, N.Y.; Richard W. Kalinoski, East Providence, R.I.

[73] Assignee: The Foxboro Company, Foxboro, Mass.

[22] Filed: Feb. 14, 1975

[21] Appl. No.: 549,929

[52] U.S. Cl. .............................................. 73/23.1
[51] Int. Cl.² ............................................ G01N 31/08
[58] Field of Search ............... 73/23, 23.1, 55, 56, 73/54, 205 D, 211; 137/624.14; 23/232 C, 232 R, 254 R

[56] References Cited

UNITED STATES PATENTS

| | | | |
|---|---|---|---|
| 1,506,617 | 8/1924 | Dommer | 73/23 |
| 1,633,352 | 6/1927 | Tate | 73/23 |
| 1,963,011 | 6/1934 | Albersheim et al. | 73/55 |
| 2,951,361 | 9/1960 | Fuller | 73/23.1 |
| 3,086,386 | 4/1963 | Kapff | 73/23 |
| 3,779,069 | 12/1973 | Berthold | 73/23.1 |

Primary Examiner—Richard C. Queisser
Assistant Examiner—Stephen A. Kreitman
Attorney, Agent, or Firm—Parmelee, Johnson & Bollinger

[57] ABSTRACT

A gas chromatograph having a pneumatic detector adapted to produce a component concentration measurement signal that is relatively unaffected by changes in carrier flow rate. The detector includes an orifice connected in the flow stream at the output end of the chromatographic column to produce a pressure signal responsive to density. This orifice signal also responds to flow rate of the fluid passing through the column. A capillary is connected in series with the orifice to produce a second flow-responsive pressure signal which is subtracted from the orifice signal in a way to effectively eliminate changes in the final measurement output signal due to changes in flow rate while leaving the signal variations due to changes in density, i.e. concentration. The orifice and capillary pressure signals are combined subtractively by means of a balanceable force-bar arrangement to which the pressure signals are applied by bellows of predetermined relative sizes, and which is automatically maintained in balanced condition by a rebalance bellows operated by a pneumatic nozzle-flapper feedback device producing the detector output signal.

6 Claims, 6 Drawing Figures

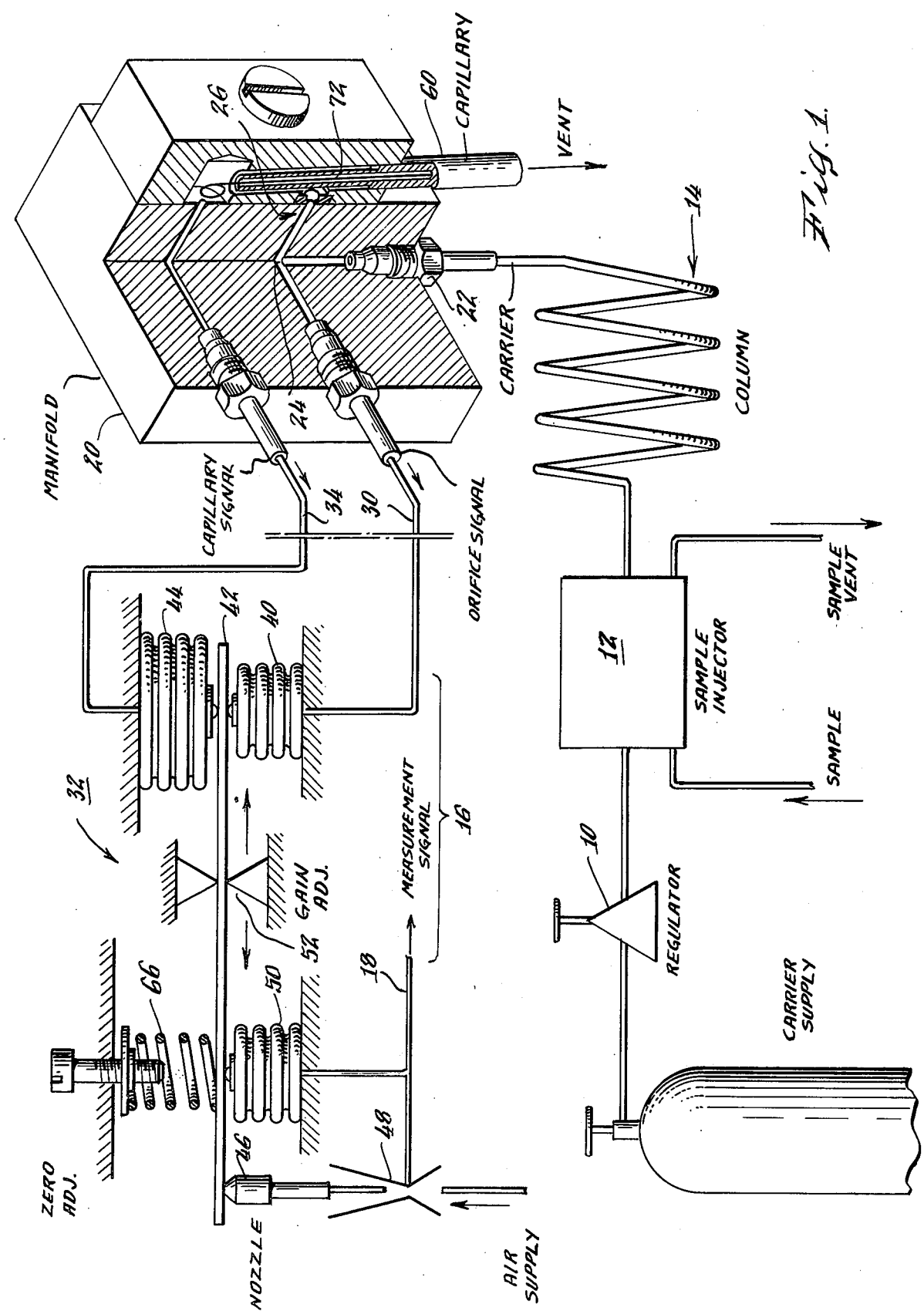

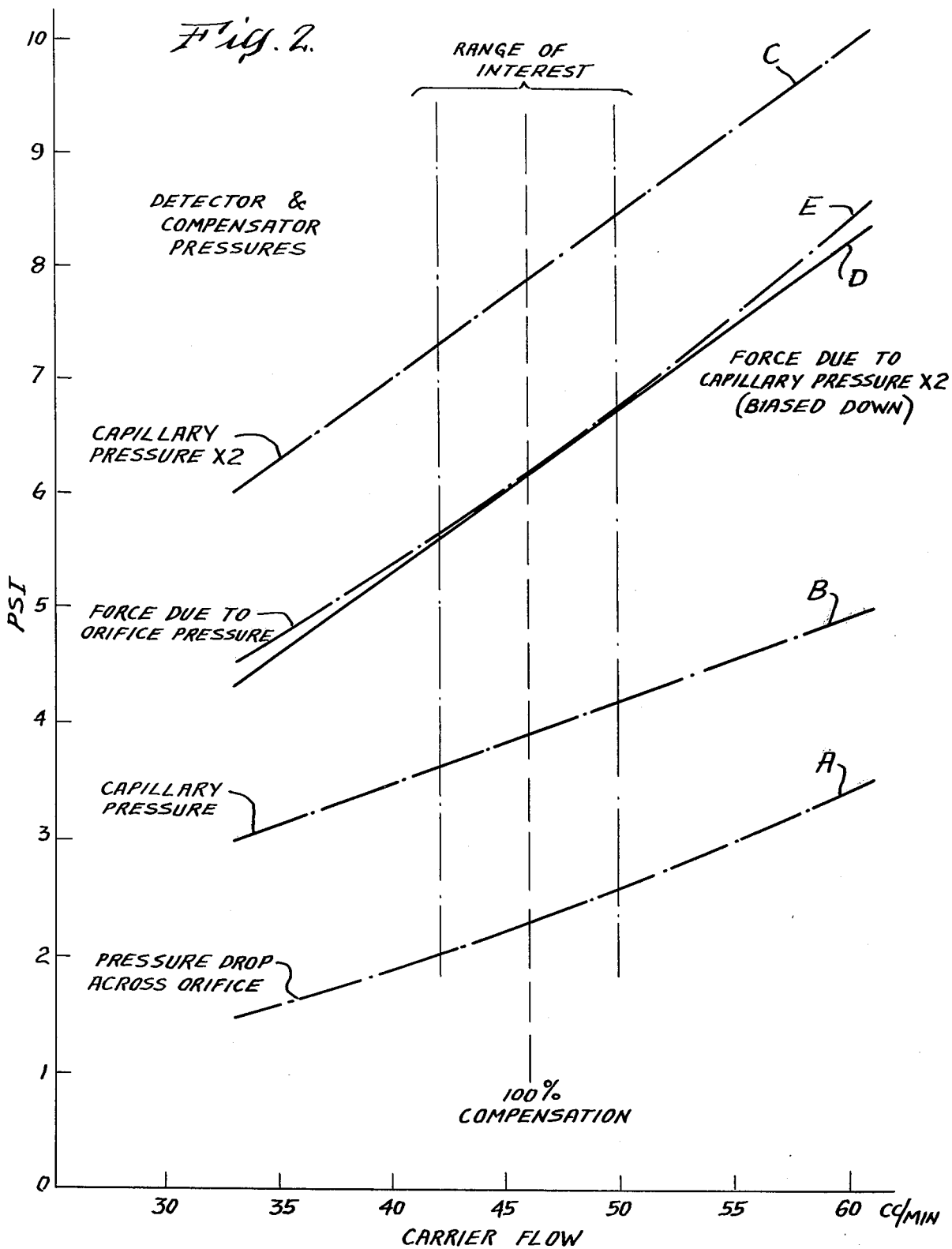

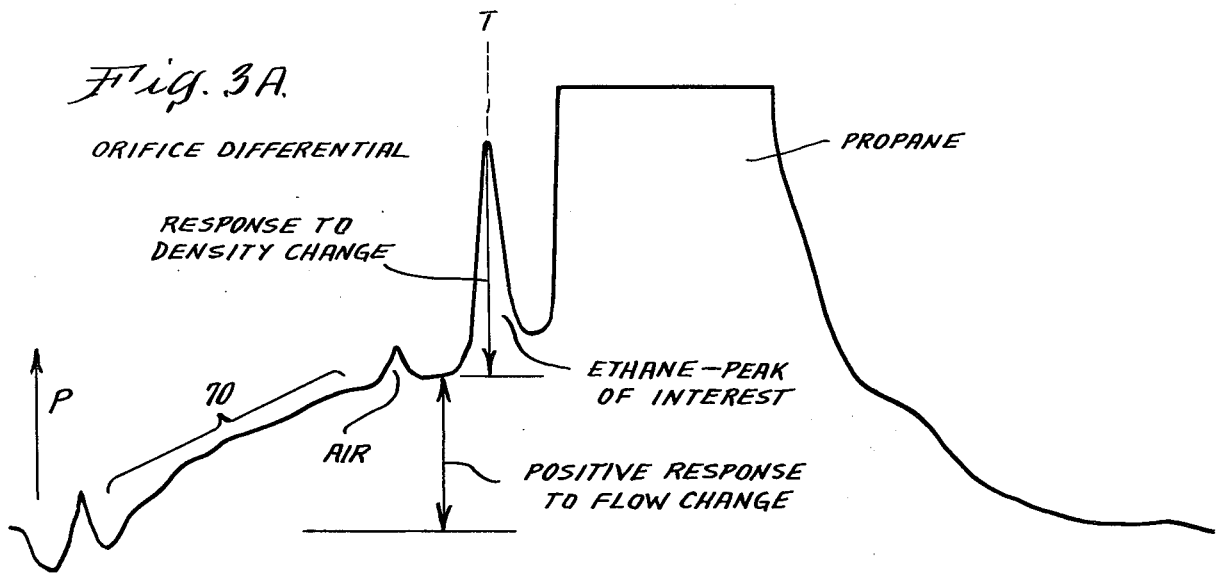
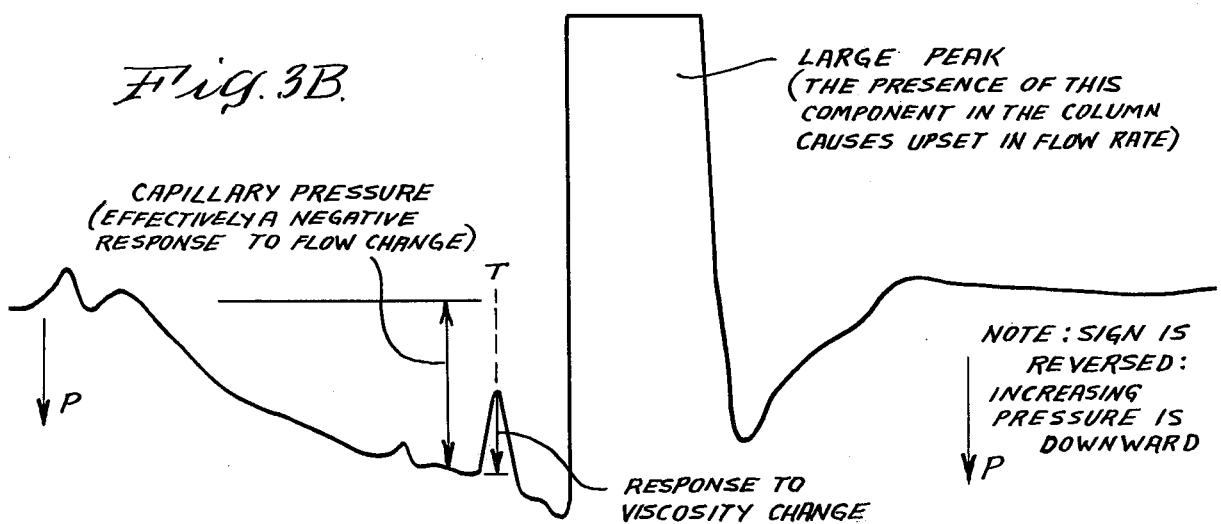
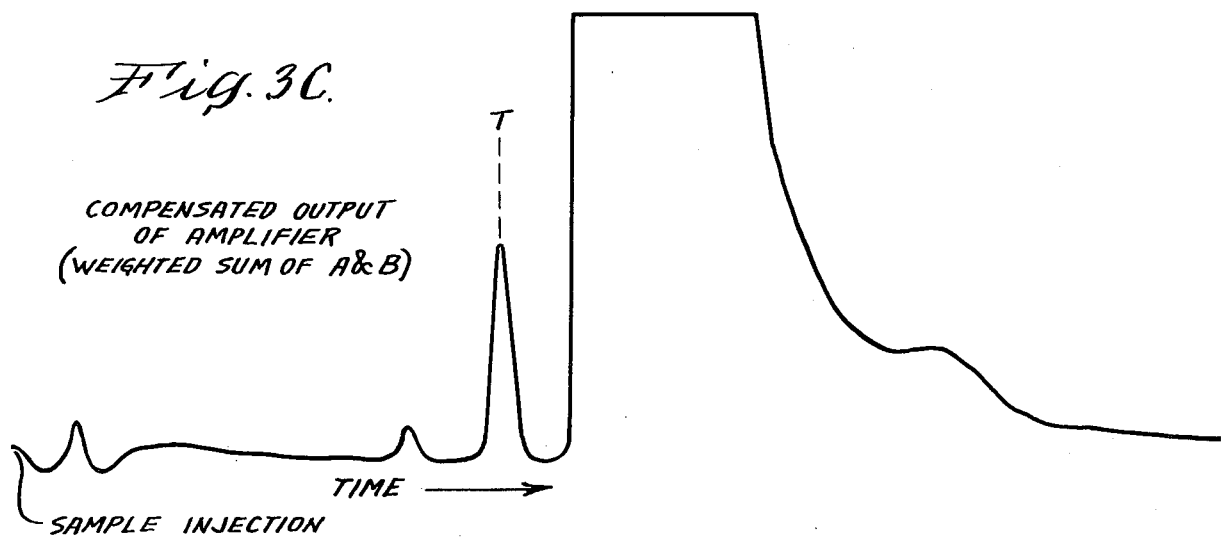

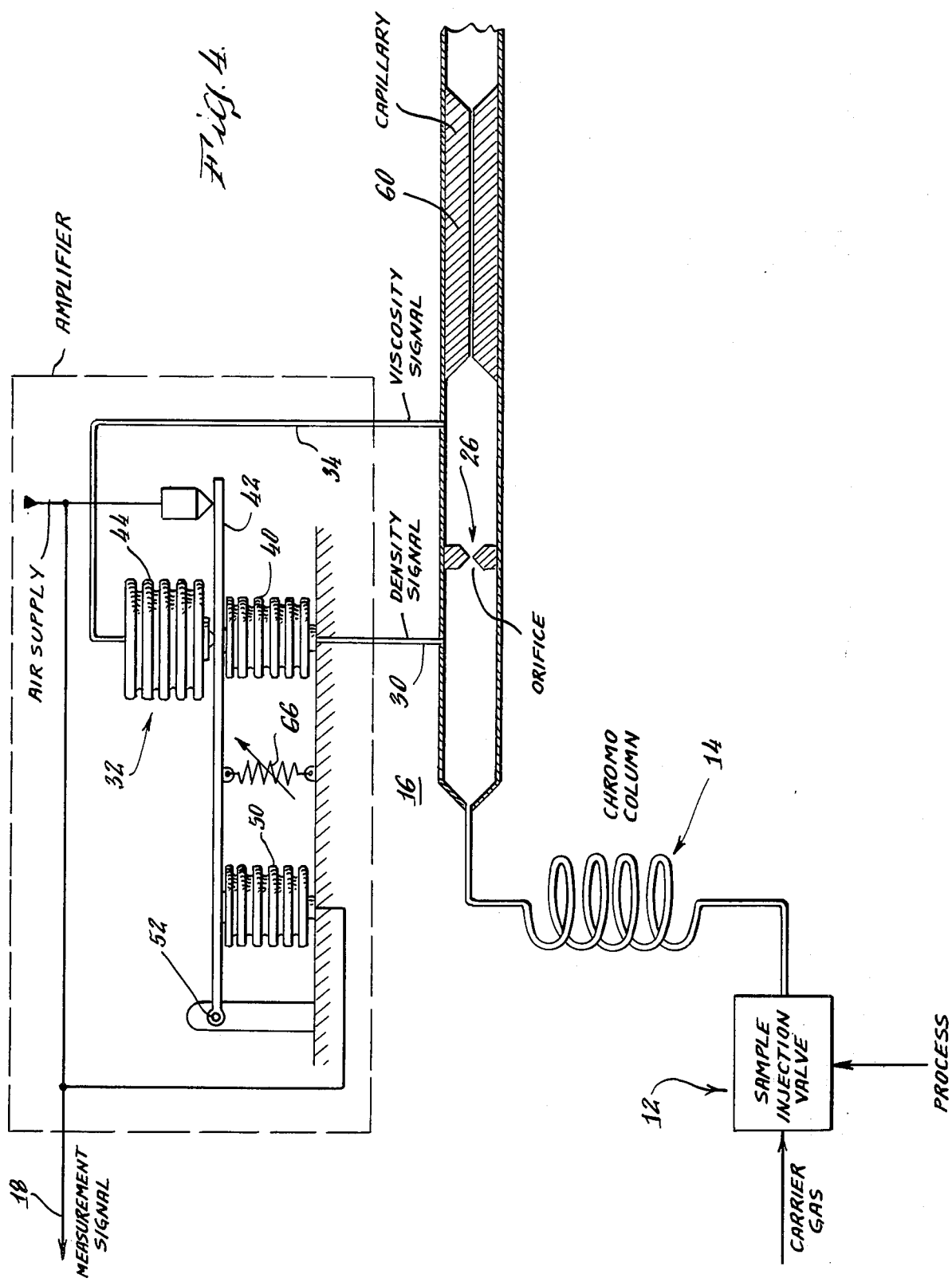

PNEUMATIC DETECTOR FOR CHROMATOGRAPHIC ANALYZER

BACKGROUND OF THE INVENTION

1. Field of the Invention

This invention relates to chromatography. More particularly, this invention relates to a detector for monitoring the output of a chromatographic column to provide signals responsive to the concentration of components separated by the column.

Chromatography is an analytical procedure wherein the components of a mixture are separated so that the individual component concentrations can be determined. In operation, a sample of the mixture is conducted by a carrier fluid through a column containing a material which retains the mixture components for differing periods of time so that the components are physically separated to emerge at different times from the column. By providing a suitable detector at the output end of the column, measurement signals are developed responsive to component concentration. Such signals may be used to develop a so-called chromatogram comprising a series of time-separated signal peaks each having a height corresponding to the concentration of a respective component.

This invention relates to an improved chromatographic detector, and particularly to detection means suitable for use in a so-called process chromatograph. A process chromatograph is one which is utilized directly with an industrial process to continuously monitor the concentration of a limited number of components (frequently just one). Such chromatograph operates continuously to analyze a series of sequential samples to develop a corresponding series of signals indicating the concentration of the component(s) of interest. The resulting output of the chromatograph over a number of such analysis cycles defines one or more so-called "trend" signals showing the change in concentration of the component(s) of interest with respect to time.

2. Description of the Prior Art

Chromatography has been used extensively for a number of years for component concentration analysis, and a wide variety of different types of detectors have been proposed for producing signals responsive to concentration of the separated components. Some of these detectors have gone into extensive commercial use for laboratory type analyses, particularly the thermal-conductivity cell and the flame-ionization detector. Use of such commercially available prior art detectors for process chromatography has however posed a number of problems including cost, inadequate reliability, and potential danger to the process itself.

Other types of detectors have been suggested from time to time, but have not been found to be satisfactory. For example, U.S. Pat. No. 3,354,696, issued Nov. 28, 1967, teaches the use of means responsive to pressure drops developed by a bridge network of pneumatic resistors connected to the output of the column. The pneumatic resistors may either be capillaries, which are used to detect changes in gas viscosity, or screens, which detect changes in gas density. Another somewhat similar detector arrangement, using a pair of capillaries to develop pressure drops, is shown in an article published in Transactions of the Faraday Society, line 63, number 8, pages 1895–1905, 1967.

A major problem associated with proposed pneumatic detectors of the type referred to in the preceding paragraph is that the pressure signal produced by a pneumatic resistor is highly responsive to the rate of fluid flow through the resistor. Thus, variations in flow velocity through the chromatographic column cause changes in the effective base line of the measurement signal, tending to cause errors in the final measurement.

It has been proposed that such errors due to changes in column flow rate be avoided by carefully regulating the pressure or flow rate at the input of the column. However, for reasons primarily related to complex column dynamics, such pressure or flow regulation has not satisfactorily solved the problem.

It also has been proposed that errors due to changes in column flow rate be compensated for, i.e. nullified, by providing a second column and detector in parallel with the primary column and detector, and connecting the two detector outputs in series opposition. By injecting the sample only into the primary column, there will be no component measurement signals developed in the secondary detector, and thus the combined primary and secondary detector signals will reflect the desired concentration measurements. If there is a change in flow rate through both columns, e.g. due to a change in the pressure of the carrier entering the columns, there will presumably be corresponding and equal flow-responsive variations in the detector output signals. Since the detector outputs are connected in series-opposition, the flow-responsive variations in the primary detector output should be nullified by the equal and opposite variations in the secondary detector output, thus leaving the component measurement signals unaffected by flow rate.

Although such a dual-column compensation system apparently would be satisfactory if the flow rate changes in both columns were always equal, there are practical operating conditions under which such equality will be maintained. For example, when a sample is injected into a column, it causes a change in the flow rate within that column, particularly when the sample contains components having viscosities quite different from that of the carrier, and thereby at once alters the base line of the detector signal. As each separated component emerges from the column, and thus is no longer present in the column to affect the flow rate, there is a corresponding step-change in the flow rate of fluid past the detector, with a consequent step-change in the detector signal base line. Because no sample is injected in the secondary column, such changes in the primary detector signal are not duplicated in the secondary detector, and therefore the secondary column and detector cannot compensate for the errors in the primary detector signal. Consequently, the dual-column compensation approach has not provided a satisfactory solution to the problem.

SUMMARY OF THE INVENTION

In a presently preferred embodiment of the invention, to be described hereinbelow in detail, a gas chromatograph is provided with a detector which comprises an orifice connected in the column output to produce a differential pressure signal responsive to fluid density, and thus responsive to component concentration. Such an orifice detector arrangement, without more, is highly sensitive to changes in flow-velocity, since the pressure drop across an orifice is proportional to $\rho V^2$.

where $\rho$ is density, and V is velocity. The effect of this flow sensitivity is, however, for practical purposes eliminated by a compensating arrangement comprising, in the preferred embodiment, a capillary tube connected in series with the orifice. This capillary tube produces a flow-responsive pressure signal which is subtracted from the orifice signal in a way which effectively avoids any significant changes in output signal baseline with changes in flow rate. The capillary pressure signal is essentially non-responsive to the density characteristic sensed by the orifice detector (as will be explained more fully below). Therefore, the concentration-related variations of the orifice pressure signal are not nullified by the capillary signal, and thus remain to provide the desired measurement signal from the chromatograph.

Accordingly, it is a principal object of the present invention to provide improved chromatographic detection apparatus and techniques. Other objects, aspects and advantages of the invention will in part be pointed out in, and in part apparent from, the following description considered together with the accompanying drawings.

BRIEF DESCRIPTION OF THE DRAWINGS

FIG. 1 shows, partly in perspective and partly in schematic form, a chromatographic system including a detector in accordance with the present invention;

FIG. 2 is a graph showing the relationship between the orifice and capillary pressures as a function of carrier flow velocity;

FIGS. 3A, 3B and 3C are graphs illustrating the manner in which certain pressure signals change as a function of time during a measurement cycle; and FIG. 4 is a pictorial representation of the system of FIG. 1.

DETAILED DESCRIPTION OF A PREFERRED EMBODIMENT

Referring now to the lower left-hand corner of FIG. 1, a carrier gas such as helium flows through a pressure regulator 10 to a conventional sample injection valve 12 which is operated at intervals to insert into the carrier gas a small pre-set quantity of a gas mixture to be analyzed. The carrier gas with the sample flows through the usual chromatographic column 14 containing a material adapted to detain the components of the sample for differing periods of time and thereby effect physical separation of the components. At the output of the column, the components emerge sequentially to be analyzed separately by a detector generally indicated at 16.

This detector 16 develops on an output conduit 18 a pneumatic measurement signal having a pressure proportional to the density of the gas emerging from the column 14, and hence of the separated components. The measurement signal thus comprises a series of successive peaks of which the magnitudes (heights) represent the concentrations of the sequentially eluting components of the sample mixture.

The detector 16 includes a manifold 20 into which the gas flow from the column 14 is directed through a fitting 22. Within the manifold, the gas flow from the column passes through a T-junction 24 to an orifice 26 (see also FIG. 4) which basically consists of a relatively sharp-edged and longitudinally-short restriction placed in the flow path of the gas. As is well known, the pressure drop across an orifice can for most purposes be considered to be proportional to the density of the gas multiplied by the square of the flow velocity (i.e. $\rho V^2$). Thus, the orifice 26 serves as the primary detector sensing device to produce a density-responsive output signal reflecting the concentration of the components separated by the column.

The pneumatic density-responsive output signal is developed at the upstream side of the orifice 26, and is directed through a conduit 30 to a pneumatic amplifier generally indicated at 32. This amplifier also receives from a second conduit 34 a pneumatic compensation signal developed in a manner to be explained below. The amplifier subtractively combines the two pneumatic signals to produce at output conduit 18, by means of a pneumatic rebalance feedback arrangement to be described, the desired measurement signal proportional to concentration of the component of interest and free from significant baseline variations due to changes in flow velocity through the column.

In more detail now, the pneumatic amplifier 32 comprises a first bellows 40 connected to conduit 30 and arranged to apply to the underside of a pivotally mounted elongate bar 42 a force corresponding to the upstream orifice pressure. The pressure downstream of orifice 26 is coupled by conduit 34 to a second bellows 44 producing on bar 42 another force tending to oppose the force of bellows 40. A pneumatic nozzle 46 senses the position of the force-bar 42 and, together with an associated venturi-type "aspirator" 48 (see for example U.S. Pat. No. 3,574,486) supplies a corresponding pneumatic signal to a feedback circuit including a feedback bellows 50 which applies a rebalance force to the bar 42 to maintain the bar in balance with respect to the pivot point 52. The air pressure in bellows 50 required to maintain this balance serves as the concentration measurement signal, at output conduit 18.

If the bellows 40 and 44 were of equal effective areas and directly opposite, the net force applied by both bellows to the force-bar 42 would be directly proportional to the pressure drop across the orifice 26, and thus would provide a measurement signal at output conduit 18 directly corresponding to component concentrations. However, such signal would be extremely flow-sensitive. That is, variations in the flow velocity of the gas passing through the orifice 26 would cause corresponding variations in the base line of the pressure signal from the orifice and thus introduce errors in the measurement. For example, changes in gas flow rate caused by the injection of sample mixture components having viscosities different from that of the carrier gas would result in such measurement errors.

In accordance with the present invention, the effects os such flow sensitivity in the detector sensing device 26 are compensated for by combining with the detector output signal a compensation signal which is flow-sensitive but which responds to the component concentration characteristic (in this case, density) in a manner different from the response of the detector device 26 to that characteristic. In the preferred arrangement, the compensation signal responds differently by being essentially non-responsive to the primary concentration characteristic (density). However, it should be understood that the basic requirement is that the compensation signal response to such characteristic be different from that of the primary detector signal.

The compensation signal is produced in the preferred embodiment by a second pneumatic device connected in series with the primary detector device. Specifically, the compensation device is a capillary 60 (see also FIG. 4) connected directly and closely to the downstream end of the orifice 26. At the remote end of the capillary, the gas is vented to atmosphere.

As is well known in the art, a capillary is a device persenting a quite elongate passageway of very small cross-sectional area. Such a device has rather special gas-flow characteristics governed largely by viscous forces from laminar flow at or near the capillary wall. To achieve the unique capillary effects, it is generally considered that the length of the capillary should be at least about 10 times the effective diameter, and preferably at least 30 times the effective diameter. The capillary used in the embodiment described herein has a length approximately 1000 times the effective diameter of an equivalent tubular passageway.

The pressure drop across a capillary is generally considered to be proportional to the viscosity of the gas multiplied by the flow velocity (i.e. $\mu V$). Moreover, if one assumes incompressible gas flow, the capillary pressure drop is non-responsive to density. It presently appears that for purposes of the present invention, the assumption of incompressible gas flow is a reasonable one. In any event, even if the capillary pressure drop includes a component related to gas density, the changes in capillary pressure drop due to gas density variations will differ significantly from the changes in the orifice pressure drop due to such density variations. Thus a capillary meets a basic aspect of this invention in that it can produce compensation signals which respond to the component concentration characteristic being sensed by the primary detector device (e.g. orifice) in a manner different from the response of the primary detector device to that characteristic.

To illustrate these important pressure relationships, FIG. 2 presents a series of graphs showing the effect of change in the carrier gas flow velocity on the pressures developed by the orifice 26 and the capillary 60. The numerical values shown on the abcissa and the ordinate of the graph are approximately correct for one particular system which has been built and tested.

Line A of FIG. 2 shows the pressure drop across the orifice 26 as a function of carrier flow velocity. Since this pressure drop is proportional to the density of the gas times the flow velocity raised to a power greater than one (generally considered to be a square function, or slightly less), line A is a curve. Line B is a graph of the pressure drop across the capillary 60 as a function of carrier flow velocity. Since a capillary pressure drop is proportional to the viscosity of the gas times the flow velocity, line B is straight.

The forces resulting from the orifice and capillary pressures are arranged to interact in the pneumatic amplifier 32 in such a way that the forces developed by flow-responsive pressure changes across the orifice 26 are opposed by equal and opposite forces developed by the flow-responsive pressure changes across the capillary 60. That is, the effects on the measurement signal (output conduit 18) of the flow-responsive changes in the orifice and capillary pressure signals cancel out, leaving only the concentration-responsive signals from the orifice.

This cancellation of the flow-responsive signal changes is effected in the present embodiment by arranging the pneumatic components of amplifier 32 in such a way as to set the rate-of-change of the capillary compensation signal with respect to flow rate equal to the rate-of-change of the orifice detector output signal with respect to flow rate. That is, the flow-responsive characteristic of the capillary signal, as applied to the force-bar 42, is arranged to have a slope equal to the slope of the flow-responsive characteristic of the orifice signal as applied to that force-bar. This equality is established at the center point of the range of interest of carrier flow rates. On either side of this mid-point, the two slopes will vary slightly, but are still sufficiently close to avoid significant measurement errors due to changes in flow rate.

Although various means can be employed for achieving equal slopes for the detector and compensation signals, in the disclosed embodiment the slopes were made equal by fixing the ratio of force-effectiveness of bellows 40 and 44 at a preselected value correlated to the characteristics of the capillary 60. This was specifically accomplished by using bellows of different effective areas, with the ratio of effective areas being approximately 2:1. The doubled size of bellows 44 doubles the downward force on the force-bar 42, so that the net bellows force on the bar is not simply proportional to the orifice differential pressure, as it would be if the two bellows had equal effective areas. That is, increasing the size of bellows 44 augments correspondingly the downward force caused by the pressure at the downstream side of the orifice (which pressure in reality is the pressure drop produced by the capillary), thus adding to the orifice pressure-drop force a second force proportional to the capillary pressure drop. Another way of looking at the double-area bellows 44 is to consider that it doubles the force developed by the pressure upstream of the capillary. Line C of FIG. 2 symbolically reflects such doubling, and indicates that both the slope and the absolute level have been correspondingly increased.

The amplifier 32 is provided with an adjustable zero spring 66 to offset or bias the increased force produced on the bar 42 by the double-area bellows 44. Line D of FIG. 2 shows the corresponding force including such bias. Line E adjacent line D represents the force due to the pressure upstream of the orifice. The two lines overlie one another, and are parallel, at the center point of the range of interest, providing 100% compensation at that point. That is, these two lines demonstrate the equality between the changes in force from the upstream capillary pressure and the changes in force from the upstream orifice pressure, due to changes in gas flow velocity through the detector.

When a sample of typical hydrocarbons is injected into the helium carrier flow-stream, the component of interest emerges from column 14 as a peak of higher density. This peak is detected by the orifice 26 causing bellows 40 to apply a greater force to the force-bar 42. After passing through the orifice, the component of interest produces a negative viscosity signal upstream of capillary 60 because the viscosity of the sample is (for typical hydrocarbons) less than the viscosity of the carrier gas. This negative viscosity signal in effect augments the density signal produced by the orifice. Thus the resultant force on force-bar 42 is the sum of the density and viscosity signals, since the components of force due to changes in flow velocity cancel out.

FIGS. 3A, 3B and 3C present graphs which are aligned representations of actual pressures measured as a function of time during one analysis cycle of a specific embodiment of the invention. These graphs illustrate the relationship between the flow-responsive elements of the signals, and the density-and viscosity-responsive elements of the signals.

FIG. 3A is a graph of the pressure drop across the detector orifice 26 during an analysis cycle. Prior to the start of the cycle, the sample valve 12 is filled with sample gas from the process. At the time marked "sample injection," the sample is injected into the carrier stream to be carried through the column 14. The initial pressure pulse variations are the result of the flow disturbance due to the motion of the valve.

The beginning portion 70 of the FIG. 3A graph shows a rise in pressure drop across the orifice 26 due to the flow change caused by the injection of a sample having a significant component which tends to flow through the column at a faster velocity than the carrier does by itself. The orifice pressure change at this time does not reflect any reading of the concentration of the component of interest, but instead represents an effective change of the base-line level of the orifice signal. This can be seen by comparison with FIG. 3B which shows the pressure drop across the capillary 60 (after amplification by bellows 44). Following injection of the sample, the capillary pressure drop changes during period 70 almost exactly the same amount as in FIG. 3A (but in the opposite direction, as presented on the graphs) as a result of the carrier gas flow velocity change due to injection of the sample.

However, at time T on both graphs, it can be seen that the orifice and capillary pressure signals change as a result of the passage of the component of interest through the detector. The orifice signal goes positive, whereas the capillary signal goes negative because of the lower viscosity of the typical sample relative to the carrier. (Note: The variations in orifice and capillary pressures are shown in reversed direction in FIGS. 3A and 3B to reflect the subtractive combining of the orifice and capillary signals by the pneumatic amplifier 32.) When these signals are combined, as shown in FIG. 3C, the resultant measurement signal has a relatively stable base line from injection to time T. The peak shown at T in FIG. 3C therefore is a combination of the orifice signal and the capillary signal without the effects of flow change. This peak corresponds to the resultant force applied to force-bar 42, so that the output signal is proportional to the density/viscosity signal developed by the component of interest without any significant error due to fluctuations in the signal baseline due to fluctuations in flow velocity.

Although the carrier gas flow change shown in FIGS. 3A through 3C is caused by the injection of a sample, it should be noted that other carrier flow changes due to, for example, a change in pressure of the carrier gas will also be compensated by the same mechanism.

In addition to avoiding errors caused by flow changes due to variations in the carrier flow rate and to sample injection, the compensation arrangement of the present invention also prevents peak distortion that would otherwise result from so-called "dead-space" or "side-capacitance" upstream of the orifice 26. Such dead space would include the volume of the conduit connecting the chromatograhic column 14 to the detector, the volume within the manifold 20 upstream of the orifice, the volume within conduit 30, and the volume of bellows 40. All such volumes would normally act as side capacitance, distorting the signal produced in bellows 40 because flow out of the column must fill the various side capacitances as the pressure peak passes from the column to the orifice. Thus the leading edges of the peak is delayed while the dead-space volumes are being filled, and similarly the trailing edge of the peak is flattened out as the dead spaces empty, following passage of the pressure peak. When the present compensation arrangement is used, however, such filling and emptying of the side capacitances appear to the detector 16 as changes in flow and, as explained above, the effects of change in flow are automatically nullified by the compensation signal developed by the capillary 60.

The orifice 26 can conveniently by a miniature jewel orifice, such as one made of synthetic sapphire, and having a circular opening of 0.0024 inches in diameter. The capillary can conveniently be tubing of 0.011 ID and a length of several inches. A flexible wire 72 of about 0.009 OD is inserted into the tubing, leaving a small annular space between the adjacent walls to serve the capillary function. The longitudinal depth of insertion of the wire into the tubing can be set for desired capillary response characteristics to match the preselected ratio of effective areas of the opposed bellows 40 and 44, so as to achieve optimum compensation, as determined by calibration tests at the time of check out. The upper end of the wire can then manually be bent, as shown, to hold the wire in its set position.

The pneumatic amplifier 32 may take any of various forms using well-known technology. The pivot point 52 is shown in FIG. 1 as adjustable to illustrate that the gain of the amplifier can be altered to suit specific conditions of different applications. Adjustment of the gain of such a force-balance arrangement can if desired be effected in various mechanically appropriate ways, for example by means of an angularly shiftable flexure reaction structure as described in U.S. Pat. No. 3,371,862.

Although a preferred embodiment of the present invention has been described in detail, it is desired to emphasize that this is for the purpose of illustrating the principles of the invention, and should not necessarily be construed as limiting of the invention since it is apparent that those skilled in this art can make many modified arrangements of the invention without departing from the true scope thereof.

We claim:

1. For use in a gas chromatograph including a separation column into which a sample mixture can be injected to be conducted through the column by a carrier gas so that the mixture components are physically separated to emerge from the column at different times;
    a pneumatic detector for measuring the concentration of the separated components without significant error due to variations in fluid flow rate;
    said detector comprising:
    an orifice connected to receive the gas from the column and to produce a first pressure signal responsive to gas density and to gas flow velocity;
    a capillary connected in series with said orifice to produce a second pressure signal responsive to gas viscosity and to gas flow velocity; and
    means to subtractively compare said first and second pressure signals and to develope a concentration measurement signal in accordance with such comparison;
    said comparison means includng a balanceable force bar;
    first and second pressure-responsive means adapted to apply opposed forces to said force-bar;

means connecting said first and second pressure signals to said first and second pressure-responsive means respectively;

pneumatic means responsive to small movements of said force-bar and adapted to maintain said force-bar in balance;

said first and second pressure-responsive means being arranged to provide a force-effectiveness ratio different from unity so as to obtain effective cancellation of the flow-related elements of such signals, whereby said measurement signal is not significantly affected by variations in fluid flow rate.

2. A detector as claimed in claim 1, wherein said orifice is upstream of said capillary;

said orifice pressure signal being developed at a point upstream of said orifice and directed to said first pressure-responsive means;

said capillary pressure signal being developed upstream of said capillary and directed to said second pressure-responsive means; and the force effectiveness of said second pressure-responsive means being substantially greater than the force effectiveness of said first pressure-responsive means.

3. In chromatographic apparatus of the type including a separation column through which a carrier fluid conducts a sample fluid mixture to be separated into its components as it passes through the column, the apparatus including an orifice in a line connected to the column output to serve as a detector means to produce an output signal responsive to a characteristic of the fluid sample components which characteristic is in turn proportional to concentration of such components, and wherein the output signal of such detector means also is undesirably responsive to fluid flow rate;

that improvement for minimizing the response of said output signal to changes in flow rate of the fluid passing through the column, comprising:

compensating means comprising a capillary connected in series with said orifice downstream thereof and arranged to produce a compensating signal responsive to the fluid flowing therethrough;

means for combining said output signal and said compensating signal in opposed sense to develop a sample concentration measurement signal;

said combining means including a force-balanceable member;

first pressure-responsive means coupled to the upstream side of said orifice and arranged to apply a corresponding force in one direction to said force-balanceable member;

second pressure-responsive means coupled to the juncture between the downstream side of said orifice and the upstream side of said capillary and arranged to apply a corresponding force in an opposite direction to said force-balanceable member;

means responsive to small movements of said force-balanceable member for automatically adjusting the net force applied thereto so as to maintain said member in force balance, whereby the adjustments of net force can serve to provide the concentration measurement signal; and means for setting the relative rates-of-change of said output and compensating signals with respect to changes in fluid flow rate therethrough to produce at least substantial cancellation of the effects of such changes in flow rate on said concentration measurement signal, while effecting changes in said concentration measurement signal in response to changes in said fluid sample characteristic.

4. Apparatus as claimed in claim 3, wherein said second pressure-responsive means has an effective area significantly greater than said first pressure-responsive means.

5. In gas chromatographic apparatus of the type including a separation column through which a carrier gas conducts a sample gas mixture to be separated into its components as it passes through the column, the apparatus including component concentration detector means in a conduit connected to the column output for producing an output signal responsive to a characteristic of the gas sample components which characteristic is in turn proportional to the concentration of such components;

that improvement in said concentration detector means comprising:

an orifice for producing a first pressure signal responsive to characteristics of the gas flowing therethrough;

a capillary connected in series with said orifice for producing a second pressure signal responsive to the characteristics of the gas flowing therethrough;

means for combining said first and second pressure signals in opposed sense to develop the component concentration measurement signal;

said combining means including a movable member;

first pressure-responsive means coupled to said first pressure signal and arranged to apply a corresponding force in one direction to said movable member;

second pressure-responsive means coupled to said second pressure signal to apply a corresponding force in an opposite direction to said member;

means responsive to movements of said member for automatically adjusting the net force applied thereto so as to balance the forces on said member and to produce an output signal responsive to the amount of force required to establish said balance of forces to serve as the concentration measurement signal; and means for predeterminedly setting the relative rates-of-change of said first and second signals with respect to changes in gas flow rate therethrough to produce at least substantial cancellation of the effects of such changes in flow rate on said concentration measurement signal, while effecting changes in said concentration measurement signal in response to changes in said gas sample characteristic.

6. Apparatus as claimed in claim 5, wherein the relative rates-of-change of said signals is predeterminedly set by fixing the pressure-responsive areas of said first and second pressure-responsive means to be substantially different whereby to produce forces of different magnitude from said pressure-responsive means for equal pressures thereof, and simultaneously providing the desired relative rates-of-change of said signals for substantial cancellation of the effects of changes in flow rate.

* * * * *